United States Patent [19]

Neer et al.

[11] Patent Number: 5,422,521
[45] Date of Patent: Jun. 6, 1995

[54] FOOT OPERATED CONTROL SYSTEM FOR A MULTI-FUNCTION DEVICE

[75] Inventors: Charlie Neer, Milford; Frank Fago, Mason; Marvin Watkins, Cincinnati, all of Ohio

[73] Assignee: Liebel-Flarsheim Co., Cincinnati, Ohio

[21] Appl. No.: 154,745

[22] Filed: Nov. 18, 1993

[51] Int. Cl.⁶ .................... H01H 35/00; H01H 3/14; A61C 1/02
[52] U.S. Cl. .................... 307/119; 200/86.5; 433/101
[58] Field of Search ............ 200/86.5, 61.89; 74/512, 560; 338/32 H, 200; 345/157; 364/413.01, 413.28; 433/28, 68, 72.75, 98, 101, 128; 307/112, 115, 116, 119

[56] References Cited

U.S. PATENT DOCUMENTS

| | | | |
|---|---|---|---|
| 804,595 | 11/1905 | Garhart | 318/262 |
| 1,919,968 | 7/1933 | Trabold | 74/560 |
| 2,040,672 | 5/1936 | Richter | 200/61.29 |
| 2,199,963 | 5/1940 | Romberger | 74/560 |
| 2,293,409 | 8/1942 | Smith | 200/61.29 |
| 2,384,805 | 9/1945 | Arens | 74/512 |
| 2,460,494 | 2/1949 | Eisenberg et al. | 338/128 |
| 2,482,540 | 9/1949 | Furnas et al. | 200/561 |
| 2,707,036 | 4/1955 | Hollub | 477/214 |
| 2,762,891 | 9/1956 | Hill et al. | 338/78 |
| 3,381,565 | 5/1968 | Haile | 84/444 |
| 3,399,287 | 8/1968 | Euler | 200/5 R |
| 3,536,229 | 10/1970 | Boros | 477/193 |
| 3,598,947 | 8/1971 | Osborn | 200/86.5 |
| 3,663,772 | 5/1972 | Grabel et al. | 200/86.5 |
| 3,833,782 | 9/1974 | Bartel | 200/86.5 |
| 3,841,172 | 10/1974 | Pilch | 74/512 |
| 3,916,719 | 11/1975 | Zwerenz | 74/478 |
| 3,963,890 | 6/1976 | Straihammer | 200/86.5 |
| 3,980,848 | 9/1976 | Schulz et al. | 200/86.5 |
| 3,980,849 | 9/1976 | Straihammer | 200/86.5 |
| 3,983,344 | 9/1976 | Straihammer | 200/86.5 |
| 4,064,769 | 12/1977 | Amdall et al. | 477/115 |
| 4,354,838 | 10/1982 | Hoyer et al. | 433/101 |
| 4,417,875 | 11/1983 | Matsui | 433/101 |
| 4,527,983 | 8/1985 | Booth | 440/7 |
| 4,543,569 | 9/1985 | Karlstrom | 340/539 |
| 4,558,194 | 12/1985 | Wiblin | 200/61.89 |
| 4,586,398 | 5/1986 | Yindra | 74/512 |
| 4,779,481 | 10/1988 | Natzke et al. | 74/512 |
| 4,965,417 | 10/1990 | Massie | 200/86.5 |
| 4,983,901 | 1/1991 | Lehmer | 588/237 |
| 5,091,656 | 2/1992 | Gahn | 307/119 |
| 5,300,926 | 4/1994 | Stoeckl | 345/157 |

Primary Examiner—J. R. Scott
Attorney, Agent, or Firm—Wood, Herron & Evans

[57] ABSTRACT

A foot-operated control system for use with a multi-function device includes a movable foot control device, one embodiment of the device comprising a pedal mounted on a base to pivot azimuthally with respect to the base and also downwardly in elevation with respect to the base. When the pedal is pivoted in azimuth, the foot control device provides selection signals to a selector including a function menu. The selector in turn, selects a menu segment from the function menu which corresponds to the desired function of the multi-function device. Pivoting the pedal to the left or to the right moves a menu indicator or icon through the various menu segments until the indicator indicates the segment corresponding to the desired function as indicated. The foot pedal is then returned to a central position and is moved in elevation to actuate the multi-function device to perform the selected function. Other foot-control devices besides the foot pedal device might be utilized with the control system to select and actuate a chosen function.

18 Claims, 4 Drawing Sheets

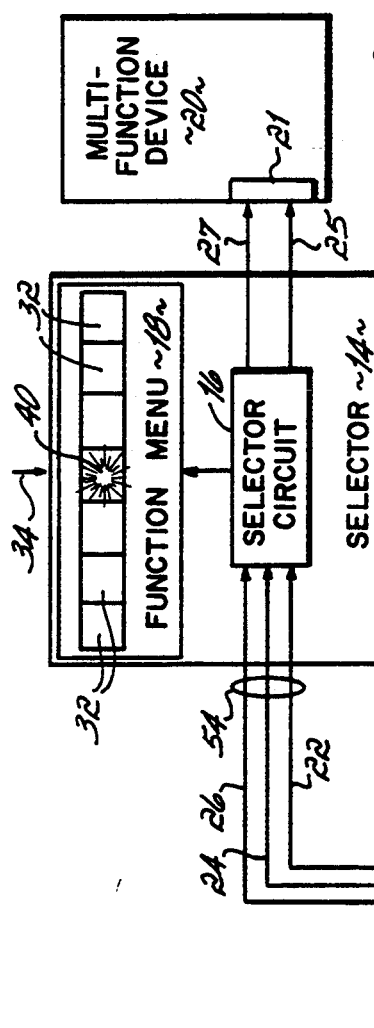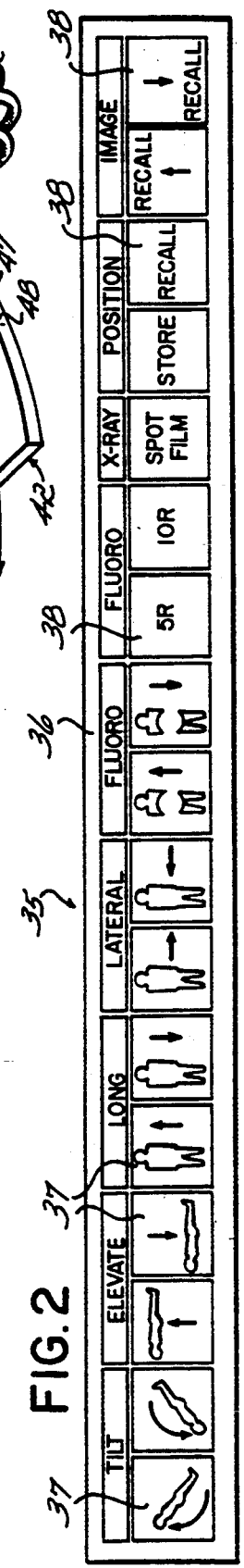

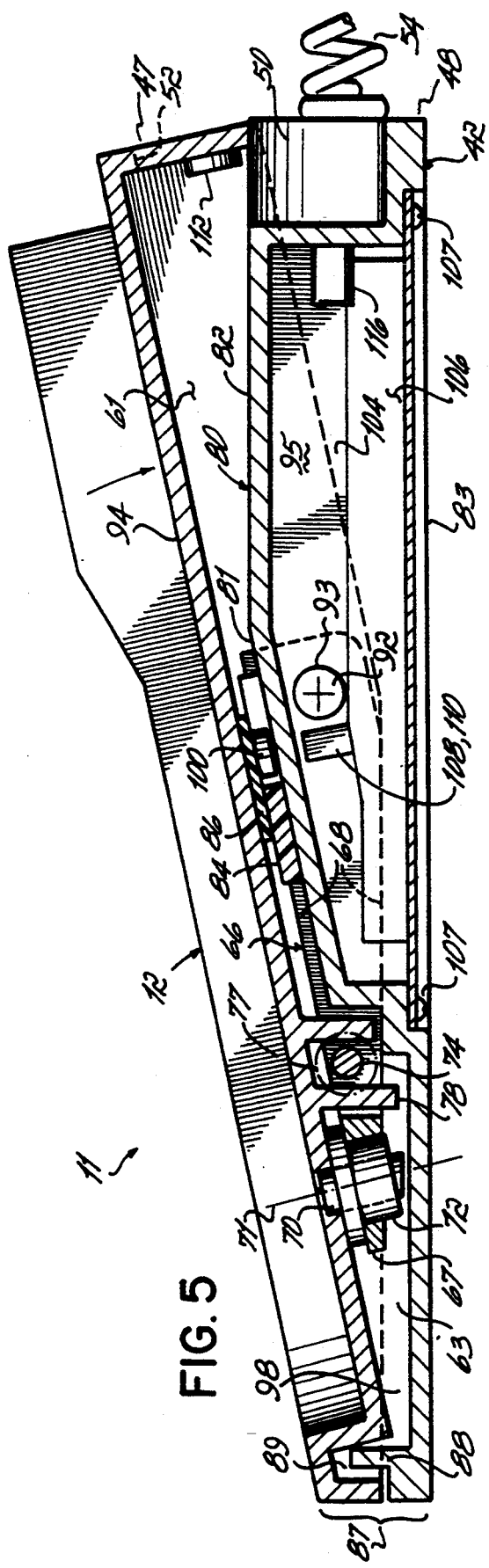
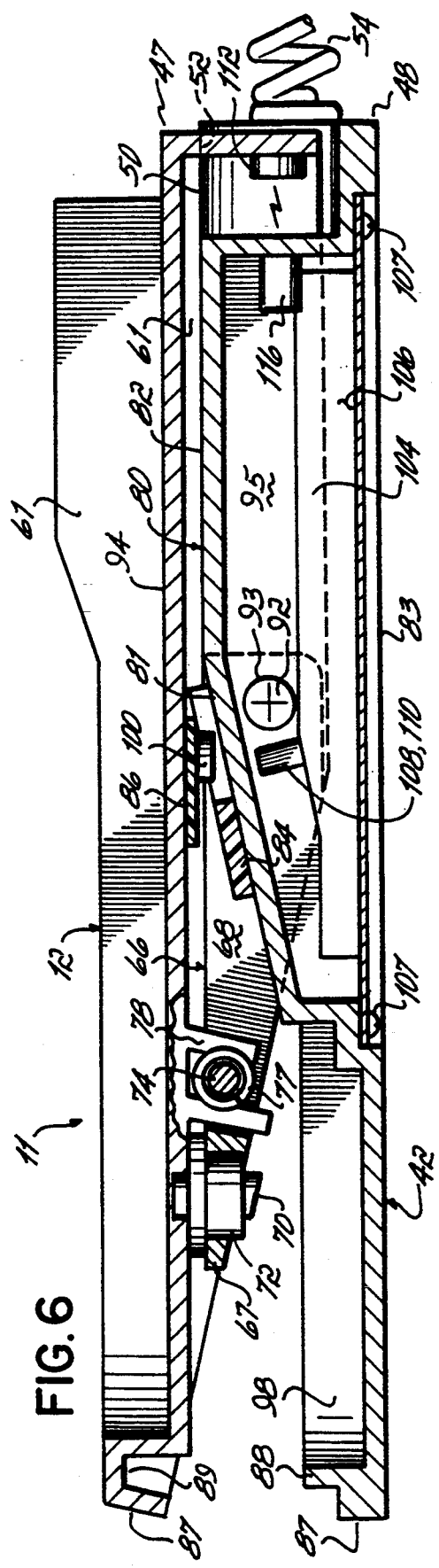

FOOT OPERATED CONTROL SYSTEM FOR A MULTI-FUNCTION DEVICE

FIELD OF THE INVENTION

This invention relates to foot-operated control systems for multi-function devices.

BACKGROUND OF THE INVENTION

Many machines and devices today are configured to perform a variety of different functions or processes. Such multi-function devices are usually equipped with some kind of control mechanism to allow a user of the device to select and actuate a particular function from the numerous available functions which the device is capable of performing. For example, one such multi-function device used today is an operating/imaging table having a patient bearing surface to hold a patient during an operation. The patient bearing surface which may be moved laterally and vertically, as well as rotated, in relation to an operating physician to place the patient in a position more convenient for access and operation by the physician. Such operating/imaging tables are equipped with x-ray, tomographic, and fluoroscopic imaging hardware systems which may be used to perform various x-ray related techniques on the patient. Such tables are operated by multi-function control systems.

One type of control mechanism for a combination operating/imaging table is a hand held unit with a plurality of buttons which are depressed to operate the various functions of the imaging hardware as well as to move the table surface in a desired direction. However, a hand-held control unit requires the physician to interrupt the ongoing medical operation to perform the task of moving the table or taking an x-ray picture of the patient. In the least, a hand-held control unit requires that one hand of the physician is free from the medical operation in order to manipulate the control unit. As may be appreciated, it is undesirable, and often impossible, for the physician to have one hand free to manipulate the hand control. Such circumstances usually arises when the surgical procedure is very precise and sensitive and interruption of the procedure is not an alternative.

In some situations it may be possible to utilize assisting medical personnel to operate the hand control unit in order to move the table and operate the imaging hardware. However, such a procedure requires additional trained personnel, increasing the cost of the operation and drawing those personnel from other more critical tasks at hand, such as assisting the operating physician with the medical operation. Additionally, the hands of the operating physician and assisting personnel are usually sterilized, and maintaining the sterility of their hands while they operate the control unit adds another difficulty to the operation scenario. Still further, it is often easier and more efficient for the physician performing the operation to be able to operate the table himself without constantly giving verbal commands for its operation to someone else.

One solution that has been offered as an alternative to a hand control unit is a foot-operated control device with a variety of buttons, pedals or joysticks which may be manipulated with the physician's foot during the operation to leave his hands free to perform the medical operation. However, foot-operated controls for multi-function devices have generally been bulky and difficult to manipulate to achieve the desired results. In general, the available foot-operated controls require various awkward movements of the user's foot to successfully achieve the desired function of the multi-function device. Furthermore, foot-operated controls for multi-function systems have generally been limited to only a few functions due to the mechanical constraints of the foot-operated control device and/or the limited range of motion of the human foot to select and actuate the various desired functions. As a result, increasing the number of functions which are selectable and actuatable with a foot control device has traditionally only been possible by increasing the complexity of the foot control, such as by adding more pedals, buttons, and/or joy sticks which must be moved or otherwise manipulated by a user's foot to produce the desired result.

Furthermore, as may be appreciated, a person who is operating a multi-function device, such as a physician moving a patient and the x-ray imaging hardware of an operating/imaging table, should stay focused upon the task at hand, e.g., the surgical operation. A control device, such as a foot-operated control, which requires the physician to constantly think about which of the multiple functions he is selecting or to continually look down at the floor to determine whether he is moving the proper pedal or button undesirably shifts the physician's concentration from his primary task, i.e., the medical operation, to the secondary task of controlling the multi-function device. Current foot-operated controls require a certain amount of trial and error in their operation, since the physician cannot be continually looking at the floor to determine proper control mechanism.

Therefore, it is an objective of the present invention to provide an improved multi-function foot-operated control system which may be easily and efficiently operated by a user to select and actuate a large number of selectable functions of a multi-function device, such as an operating/imaging table. These and other objectives will be more clearly illustrated below by the summary and detailed description of the invention.

SUMMARY OF THE INVENTION

The foot-operated control system of the present invention comprises a moveable foot control device that rests on a floor surface and is manipulated by the foot of an operator to generate selection and actuation signals. A selector is coupled to the foot control device to receive the selection and actuation signals and generate command signals to select and actuate a function of a multi-function device. The selector, in turn, is coupled to a multi-function device capable of performing various different functions in response to the selector command signals. The foot control device has a pedal that is movably mounted on a base to move in a lateral direction and provide selection signals to the selector for selecting various functions of the multi-function device. The foot pedal is movable in elevation in the central position on the base to provide an actuation signal for actuating the selected function of the device.

One embodiment of the foot-operated control system includes a foot control device with a pedal mounted to a base on a generally vertical axis so that the pedal may be rotated in azimuth with respect to the base when the operator's foot pivots from side-to-side. The pedal is azimuthally moved to overlie either the right side or left side of the base, and when the pedal is so situated, the foot control device generates a selection signal which is input to the selector. The selector, in response to the selection signal moves through a menu of selectable functions. When the desired function of the menu has been selected, the pedal is azimuthally moved back to its central position in line with the pedal base wherein movement through the function menu ceases. The pedal is preferably biased to rest in the central position in the absence of an azimuthal pivoting force by the operator's foot. The pedal is also mounted on the base to pivot downwardly in elevation when in the central position to actuate the selected function of the multi-function device.

Depressing the pedal downwardly generates the actuation signal which is also input to the selector. The selector in response to the actuation signal then provides the necessary command signals to the multi-function device to actuate the device to perform the selected function. As long as the pedal remains depressed in the downward position, the multi-function device continues to perform the selected function. In summary, the pedal is laterally moved in azimuth to the left side or right side to select a function, and pivoted downwardly in elevation to actuate the selected function.

The foot pedal unit includes an elevation movement inhibitor which prevents the pedal from being moved to the elevational down position when the pedal is pivoted to the right or left of the central position. The inhibitor also inhibits the pedal from being pivoted when the pedal is depressed for actuation. This prevents the multi-function device from being actuated when a function is being selected, and vice versa. The pedal is preferably restricted in azimuthal and elevational movement so as not to require extension of the operator's foot beyond natural side and forward pivoting motions. Therefore, the system does not require any unnatural or over-extensive motion of the foot to operate the multi-function device coupled to the control system.

The function menu of the selector includes individual menu segments which indicate the various different selectable functions. An indicator moves in one direction through the menu to indicate which menu segment is currently selected when the pedal is moved to the right side position and moves in the opposite direction through the menu when the pedal is moved to the left side position. The indicator stops moving through the menu and halts on a chosen function segment when the pedal is moved back to its central position. When the indicator shows that the desired function has been selected and the pedal is in the central position, the pedal is pivoted downwardly in elevation to actuate the selected function.

Preferably, the function menu includes a visual display with individual menu windows corresponding to each of the selectable functions, and an illumination indicator which illuminates the selected menu window to visually display the selected function menu. Each menu window graphically denotes the associated function, either pictorially or textually. The visual display is placed in the line-of-sight of the operator to allow quick visual identification of the selected function. Therefore, a quick glance allows the operator to determine which function is selected and eliminates any trial and error methods when operating the multi-function device. Holding the pedal in the left or right side position rapidly scrolls the indicator through the menu segments to speed up the process of selecting a function.

Using the foot-operated control system of the present invention, a virtually infinite number of functions might be selected to be performed by the multi-function device. Although a preferred foot pedal device is disclosed for use with the system, any variety of foot-controlled devices might be utilized to generate the necessary selection and actuate inputs to the selector. In this way, the foot-operated control system of the present invention provides a simple and efficient means for selecting and actuating various different functions of a multi-function device without requiring an inordinate amount of concentration upon the foot control mechanisms nor continual trial and error actuation of the multi-function device to verify which function has been selected. The selection menu readily visually indicates which function has been selected, while the operator performs other more important tasks. The preferred foot pedal device of the system allows the operator's foot to rest in a natural position and move slightly left, right, or downwardly in the human foot's natural range of motion to select and actuate a function of the multi-function device. Further, a virtually infinite number of functions are selectable in three simple motions, while the foot stays essentially stationary in position on the floor.

Further advantages of the foot-operated control system of the present invention are illustrated by the drawings and detailed description below.

BRIEF DESCRIPTION OF THE DRAWINGS

FIG. 1 is a schematic drawing of the foot-operated control system of the present invention;

FIG. 2 is a front view of the function display menu of the foot-operated control system in FIG. 1;

FIG. 3 is a front perspective view of the foot pedal device utilized in the foot-operated control system of FIG. 1;

FIG. 5 is a cross-sectional view of the foot pedal device taken on lines 5—5 of FIG. 1 showing the pedal in the upper position; and FIG. 6 is a cross-sectional view similar to FIG. 5 showing the pedal in the lower position.

DETAILED DESCRIPTION

Figure 4:
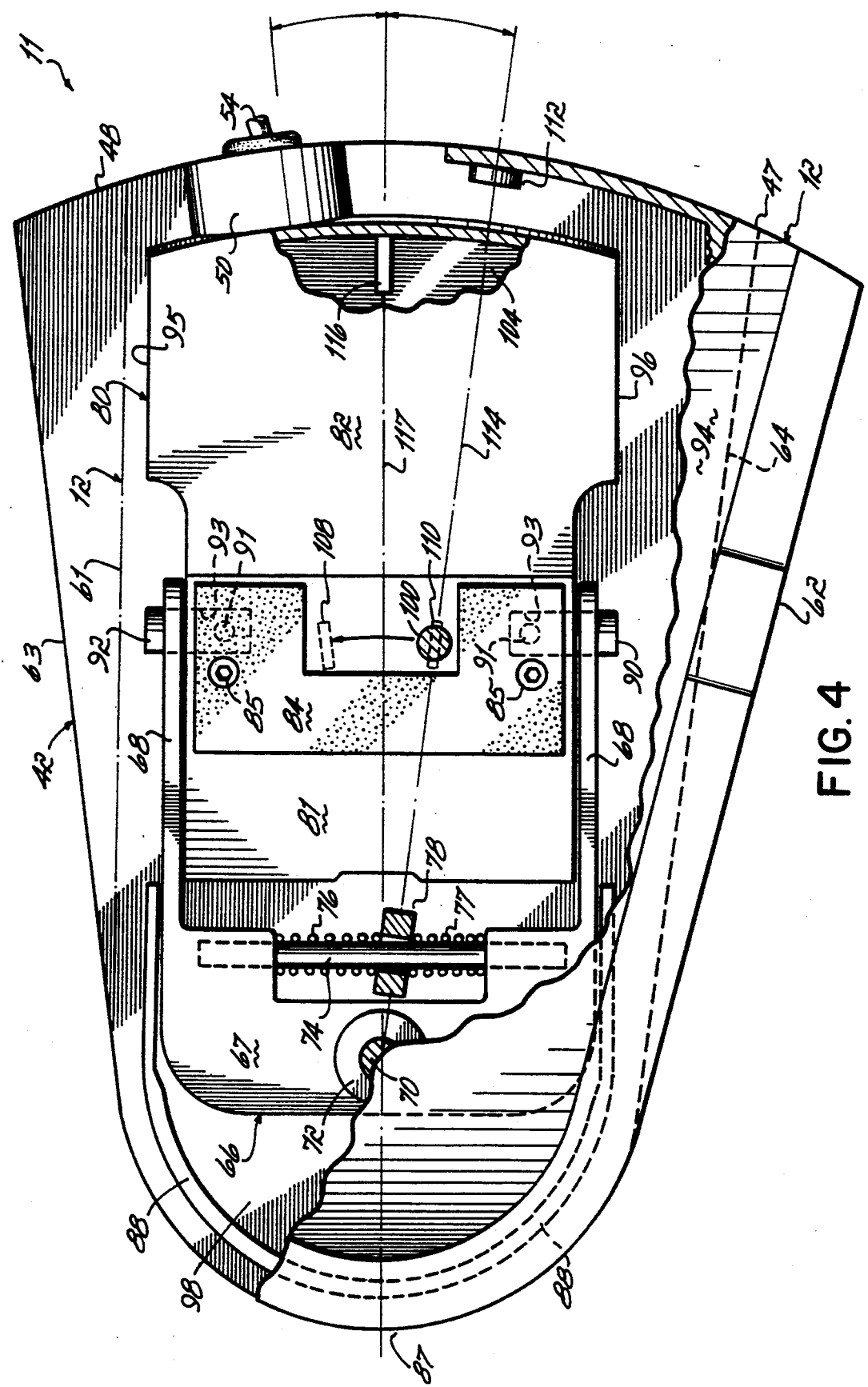
FIG. 4 is a top view of the foot pedal device of FIG. 1, partially cut away to illustrate the azimuthal movement of the pedal.

FIG. 1 is a schematic view of the foot-operated control system 5 of the present invention which is utilized to select one of a number of selectable functions of a multi-function device 20 and to actuate the device to perform the selected function. The system 5 preferably includes a foot control device 6 having a laterally and elevationally movable foot pedal 7 to be moved to generate selection and actuation signal inputs on lines 22, 24 and 26. Selector 14 receives the inputs on lines 22, 24 and 26 and generates command output signals on lines 25, 27. A multi-function device 20 capable of performing various different selectable functions is coupled to selector 14 via lines 25, 27. The multi-function device 20 might be a hospital operating/imaging table having a patient bearing table surface with various different ranges of motion and x-ray hardware with selectable x-ray imaging capabilities. For example, the patient bearing table surface might move up, down, side-to-side or rotationally (not shown). Similarly, the x-ray hardware might be able to take a simple x-ray picture, or perform a complex tomography or fluoroscopy routine. Accordingly, the multi-function device 20 has a signal receiving circuit 21 which receives the command signals on lines 25, 27 from selector circuit 16 and operates the appropriate mechanical mechanisms of device 20 to perform the selected function. Therefore, the foot pedal 12 is moved left or right to select a function and is moved in elevation when in its central position, to actuate the multi-function device 20 to perform the selected function.

Foot control device 6 is connected to selector 14, and specifically, to selector circuit 16 through a plurality of input lines 22, 24, 26, and the output of selector circuit 16 is couple to multi-function device 20 by command lines 25, 27. The foot pedal 7 of foot control device 6 is configured to move laterally to a left side position 13, to a right side position 15, or to a central position 17 as indicated in FIG. 1. When foot pedal 7 is moved to the left side position 13, it generates an input signal on line 22 and the selector circuit 16, in response to the line 22 input, selects one of the various selectable functions of multi-function device 20. Preferably device 20 will have at least three such selectable functions and the selector circuit 16 responds to input line 22 by moving through the successive functions of device 20 in one direction. Selector 14 continues selecting through the available functions so long as the foot pedal 7 is maintained in the left side position 13 or until the selector circuit 16 reaches the last available function or the foot pedal 7 is moved laterally to return it to the central position 17. Similarly, if foot pedal 7 is moved laterally to the right side position 15, an input is provided on line 24 and the selector begins selecting through the list of successively selectable functions in a direction opposite to that which is taken when the foot pedal 7 is moved to the left side position 13. Again, the selector circuit 16 continues selecting through the list of available functions until it reaches the last available function or until the foot pedal 7 is returned to its central position 17.

For purposes of illustration, the successive list of available functions might be thought of as a row of functions having a leftmost end and a rightmost end. With such a convention, system 5 selects through the list of successively selectable functions in the left direction when the foot pedal 7 is moved laterally to the left side position 13 and will cease selecting when the foot pedal 7 is returned to its central position 17 or when the selector circuit 16 has moved through the list of functions to the leftmost or last selectable function. Similarly, the selector circuit will select through the list of functions in the right direction when pedal 7 is moved laterally to the right side position 15, and the selector circuit 16 will cease selecting in the right direction when pedal 7 is laterally moved to its central position 17 or when circuit 16 reaches the rightmost or last selectable function.

Pedal 7 and selector circuit 16 might be configured such that each successive step through the list of selectable functions is accomplished only by laterally moving pedal 7 to one of the left side 13 or right side 15 positions and then returning it to the central position 17. Then to move to the next selectable function, the side movement and return to the central position 17 is repeated. However, foot control device 6 and selector circuit 16 is preferably configured such that moving pedal 7 laterally to one of the side positions and maintaining the pedal 7 at the side position will cause the selector circuit 16 to scroll continuously through each successive selectable function in the respective direction corresponding to the pedal side position. The scrolling would then stop when pedal 7 was moved to the central position or the leftmost or rightmost functions of the list had been reached. Alternatively, selector circuit 16 might be designed with a wraparound feature so that it jumps from the rightmost function to the leftmost function and vice versa when either end of the function menu is reached, and the pedal 7 is still moved to one side of the foot control device 6. Accordingly, once the desired function has been selected, the foot pedal 7 is returned to the central position and moved downwardly in elevation to actuate the selected function. The device 20 continues to perform the selected function until the pedal is returned to the elevational up position as will be described further hereinbelow.

Selector 14 includes a function menu 18 which is controlled by selector circuit 16 via line 30. Function menu 18 includes a plurality of menu segments 32, each of which corresponds to at least one of the selectable functions that is available with multi-function device 20. Menu 18 includes an indicator 34 of some kind which indicates which of the selectable menu segments 32 has been selected using foot control device 6 and selector circuit 16. Function menu 18 and indicator 34 are humanly perceptible and preferably include a visual display menu and a visual indicator which allows an operator to quickly determine the function which he has selected. For example, referring to FIG. 2, one embodiment of the function menu 35 might include a translucent plate 36 having a plurality of pictorial segments 37 or textual segments 38 to indicate which of the selectable functions has been selected. Menu 35 also includes an icon 40 (FIG. 1) to visually indicate the selected function. For example, the icon 40 might simply be a back light device which illuminates the selected window segment of translucent plate 36. The plate 36 of FIG. 2, for example, illustrates various selectable functions related to movement of the patient bearing surface of an operating table or related to operation of the x-ray imaging hardware of an operation/imaging table. Various other pictorial menu segments 37 or textural segments 38 may be utilized for various other multi-function devices depending on the types of functions that are selectable.

A preferred embodiment of the foot control device of the present invention is shown in FIG. 3 wherein foot control device 11 includes a foot pedal 12 which is mounted to a base 42 for azimuthal and elevational pivoting movement thereon. Specifically, pedal 12 may be laterally pivoted in azimuth to a left side position, as indicated by arrow 44, which overlies the left side of base 42 as indicated in phantom lines 41 in FIG. 3. Similarly, pedal 12 may be pivoted in azimuth to a right side position as indicated by arrow 45 to overlie the right side of base 42 as shown by phantom lines 43 in FIG. 3. When foot pedal 12 is returned to the central position as it is shown in FIG. 3, it may be pivoted downwardly in elevation as indicated by arrow 46 such that the front end 47 of pedal 12 is juxtaposed with the front portion 48 of base 42.

Control device 11 is incorporated into the foot-operated control system 5 of FIG. 1. When pedal 12 is moved downwardly in elevation in its central position after a function has been selected, control device 11 generates an actuation input signal on line 26 to selector circuit 16. The selector circuit 16 then generates a command signal or command sequence on command lines 25, 27. The command sequence actuates the multi-function device 20 to perform the mechanical or other function that has previously been selected by lateral movement of pedal 12. That is, when foot pedal 12 is pivoted downwardly, the command sequence on lines 25, 27 indicates that the device 20 is to perform the selected function. The command sequence on lines 25, 27 might be any available standard control sequence, such as an HPIB bus command or RS 232 series command, for example, or any other signalling sequence which is compatible with the signal receiving circuit 21 of the multi-function device 20 being controlled. Further, lines 25, 27 might contain the memory address of a series of software code commands to cause multi-function device 20 to execute a particular function. Accordingly, the present invention is not to be limited to any particular control commands or sequence of commands for actuating the multi-function device 20.

The foot control device 11 utilizes a movement inhibitor to prevent pedal 12 from being moved in elevation when the pedal 12 is moved laterally away from the central position 17 to one of the left or right side positions 13, 15. As shown in FIG. 3, base 42 of foot control device 11 has an upwardly extending hump portion 50 which coincides with a recess 52 formed in the front end 47 of pedal 40. When pedal 40 is in its central position as shown in FIG. 3, recess 52 aligns with hump portion 50 and pedal 12 may be pivoted downwardly in elevation to actuate a selected function. However, when pedal 12 is moved to a left or right side position, the bottom edge 53 at the front 47 of the pedal on either side of recess 52, will abut with hump 50 and prevent downward pivoting movement of pedal 12. Further, when hump portion 50 is seated in recess 52, the pedal cannot be pivoted in azimuth. In this way, a function may not be actuated while the pedal 12 is pivoted to one side of the base 42 to select a function, and similarly, a different function may not be selected while the current function is being actuated because hump 50 is seated in recess 52. That is, selecting a function and actuating the device 20 to perform the selected function are mutually exclusive of one another. Cord 54 connected to device 11 contains input lines 22, 24 and 26 (FIG. 1) and is connected to selector circuit 16. The selector 14, including selector circuit 16 and menu 18 may be a separate standing unit, or may be incorporated into the housing and coupled to the circuitry of the multi-function device 20, in which case cord 54 would connect directly to the multi-function device 20.

FIG. 4 is a top view of the foot control device 11 illustrated in FIG. 3. Pedal 12 in FIG. 4 is partially cut away to show the connection between base 42 and foot pedal 12 which allows foot pedal 12 to pivot azimuthally in its elevationally upward position (FIG. 5) and to pivot downwardly in elevation (FIG. 6) in its central position. Referring to FIG. 4, foot pedal 12 defined by side perimeter lines 61, 62 and is shown in its right side position overlying the right side of base 42 which is defined by side perimeter lines 63, 64. When pedal 12 is azimuthally pivoted to overly the right side of the base 42, the right side 62 of pedal 12 extends beyond the right side 64 base 42 (shown in the bottom side of the page). To allow pedal 12 to pivot about base 42, pedal 12 is mounted to a U-shaped yoke 66 including a base portion 67 and forwardly projecting arms 68 which extend forward from the base portion 67 towards the front end 47 of pedal 12. Yoke 66 is attached to the base 42 by pins 90 and 92. Pedal 12 is attached to yoke 66 by a vertically projecting post 70 which extends into a circular bearing 72 located at the center of base portion 67 of yoke 66 (see FIGS. 5 and 6). Post 70 of pedal 12 rotates within circular bearing 72 to allow pedal 12 to pivot azimuthally with respect to yoke 66. Yoke 66 also includes a lateral bar 74 and two opposing bias springs 76, 77 which extend from one side of the U-shaped yoke 66 to the other side proximate base portion 67. Pedal 12 includes a fork 78 which extends vertically downward from the pedal (See FIGS. 5 and 6). The prongs of fork 78 partially surround lateral bar 74 and are sandwiched in between the opposing bias springs 76, 77. Bias springs 76, 77 act against fork 78 to bias foot pedal 12 to a central position with respect to yoke 66 and base 42. In this way, when no pivoting force is applied to pedal 12 by the operator's foot, the pedal 12 moves back into the central position with respect to yoke 66 and base 42 under the force of springs 76, 77.

When pedal 12 is in an elevationally upward position as shown in FIG. 5, it may be pivoted in azimuth around a vertical axis 71 defined by post 70 and bearing 72 to overlie the right or left side of the base 42. Forward of fork 78, base 42 includes an upward by extending ridge section 80 with a planar sloping portion 81 which slopes gradually up to a planar horizontal portion 82 where it levels off and extends generally parallel with the flat bottom 83 of base 42. When the pedal 40 is in an elevationally up position (FIG. 5), the pedal 40 is in a plane generally parallel the plane defined by sloping portion 81, and when the pedal 12 is in an elevationally down position (FIG. 6), the pedal is in a plane parallel the plane of horizontal portion 82. Preferably a short saddle or bearing block 84 is attached to the sloping portion 81 of ridge section 80. Saddle 84 is preferably a low friction material, such as Teflon, and is mounted to sloping portion 81 by a couple of screws 85 (FIG. 4). Additionally, pedal 12 includes a low friction shim or bearing plate 86 of the same or a similar material as that of bearing block 84. When pedal 12 is mounted on top of base 42, shim 86 is juxtaposed and in contact with bearing block 84. Pedal 12 may then be smoothly pivoted in azimuth on base 42 to select a function due to the low friction contract between shim 86 and block 84.

At the rearward end 87 of foot control device 11, base 42 includes an upwardly extending U-shape flange 88 which fits within a corresponding U-shaped cavity 89 on the pedal 12. When pedal 12 is in the elevational up position the heel end of the pedal 12 touches the base while the front end 47 of pedal 12 is suspended above base 42. (See FIG. 5.) In the position of FIG. 5, flange 88 fits within cavity 89 such that when the pedal 12 is pivoted in azimuth, the heel end 87 of the pedal remains restricted from side-to-side motion while the front end 47 of pedal 12 sweeps in a radial arc about post 70. That is, the heel end 87 of foot pedal 12 remains generally stationary with respect to the base during azimuthal pivoting so that only the front end 47 of pedal 12 overly pivots to the left or right side of base 42 (See FIG. 3 and 4).

Pedal 12 has opposing side walls 61, 62 wherein a portion of the walls extend downwardly from a flat foot-contacting surface 94. The downward portions of side walls 61, 62 prevent the pedal 12 from being azimuthally pivoted too far to either of the side positions because they contact the sides of ridge section 80. As seen in FIG. 4, the side wall 61 will strike a side wall 95 of ridge section 80 when the pedal 12 is pivoted to its rightmost position to prevent any further right pivoting of the pedal. Similarly the wall 62 of pedal 12 strikes the right side wall 96 of ridge section 80 when the pedal is pivoted to its leftmost position. A portion of the pedal side walls 61, 62 also extend upwardly above foot-contacting surface 94 to confine and contact the operator's foot when it is pivoted in order to move pedal 12 to the left or right. To accomplish the elevational pivoting motion of pedal 12 with respect to base 42, two opposing pivot pins 90 and 92 are inserted through the arms 68 of yoke 66 and into the ridge 80 of base section 42, as best shown in FIG. 4. Two opposing apertures 93 are formed in opposite sides of ridge section 80 to receive pivot pins 90, 92 which are secured to the base portion 42 by securing screws 91 which extend against the pins from the bottom side 83 of base 42. Referring to FIG. 6, the yoke 66 is pivoted upwardly and downwardly about pins 90, 92 and about ridge section 80 when pedal 12 is pivoted. When pedal 12 is in the elevationally down position, the foot-contacting surface 94 is generally horizontal and parallel with the flat portion of ridge 80 and the bottom 83 of base 42.

As discussed hereinabove, pedal 12 may not be pivoted downwardly in elevation unless the pedal 12 is in its central position and hump 50 aligns with recess 52 of pedal 12 (See FIG. 3). Referring to FIG. 6 when pedal 12 is pivoted downwardly, the entire azimuthal pivoting structure including yoke 66 bearing 72, post 70, lateral bar 74, bias springs 76, 77 and fork 78 all move upwardly away from a recess 98 formed within base 42 by ridge section 80 and the U-shaped flange 88. In the preferred embodiment of the foot control device of the present invention the pivoting pins 90, 92, which allow the pedal 12 to pivot in elevation, are positioned such that a majority of the weight of pedal 40 is rearward of the pins 90, 92. In this way, when no elevational pivoting force is applied on surface 94 by the operator's foot to move pedal 12 to the elevationally down position, gravity maintains the pedal in its' unpivoted elevationally up position as shown in FIG. 5. In that way, there is no additional elevational biasing structure necessary for the foot pedal 12 to rest in the unactuated position.

To generate the input signals to the selector 14, a preferred embodiment of the foot control device 11 utilizes magnetic elements and magnetic proximity switches to generate the selector input signals on lines 22, 24 and 26. Specifically, referring to FIG. 5, a magnetic element 100 is mounted to foot pedal 12 proximate the center of the pedal to be juxtaposed with the sloping portion 81 of ridge section 80 of the base 42 and a magnetic element 112 is mounted at the front 47 of pedal 12. The ridge section 80 defines a cavity 104 in base 42. Cavity 104 is closed at the bottom of base 42 by a circuit board 106 which is mounted to base 42 by screws 107 or other appropriate fastening means. Circuit board 106 contains at least three magnetic proximity switches 108, 110 and 116 and any supporting circuitry necessary for operation of control device 11 and switches 108, 110, 116. The switches 108, 110 and 116 are positioned in cavity 104 such that movement of the magnetic elements 100, 112 located on pedal 12 will activate the proximity switches and generate selection and actuation inputs on lines 22, 24 and 26. For example proximity switches 108 and 110 are located on the circuit board 106 to be at the center of base 42 near the sloping portion 81 and magnetic element 100. (See FIG. 4) When pedal 12 is pivoted in azimuth to the left side position, magnet 100 is proximate to magnetic proximity switch 108 and magnet 100 activates the switch to generate an input to the selector circuit 16. Similarly, when the pedal 12 is pivoted to the right side position, magnetic element 100 is proximate to switch 110 to generate another selection input. The selection inputs generated by switches 108, 110 on lines 22 and 24, in turn, are input to selector circuit 16 which moves indicator 34 through function menu 18 to select a desired function. The material of base 42 is preferably nonmagnetic such that the proximity switches 108, 110 are actuated by sensing a magnetic field from magnetic element 100 which extends through the wall of sloping portion 81. In this way, there is no contact necessary between magnetic element 100 and the appropriate switches 108, 110 and one magnetic element may be used to actuate both switches. There is preferably approximately a one inch spacing between proximity switches 108, 110 such that when the magnet 100 is in one of the side positions to actuate the proximity switch corresponding to that side position, it does not effect nor actuate the magnetic switch of the opposite side position. Further, when pedal 12 is in the central position, the magnet 100 does not activate either switch, 108, 110.

A similar magnetic element and magnetic proximity switch is used to generate an actuation input on line 26 when the foot pedal 40 is pivoted downwardly in elevation in its central position. Referring to FIGS. 4, 5, and 6 it may be seen that magnetic element 112 is fixed to the downwardly extending front side 47 of pedal 12. Magnetic element 112 is placed on longitudinal center line of pedal 40 as illustrated by line 114 in FIG. 4. The magnetic proximity switch 116 is located on the center line of base 42 as illustrated by line 117 in FIG. 4. When pedal 12 is in its central position, line 114 aligns with line 117 and the magnetic element 112 is in longitudinal alignment with magnetic proximity switch 116. As seen in FIG. 5, when the pedal 12 is in the elevational up position, the magnetic element 112 is not adjacent to magnetic proximity switch 116 and switch 116 is not activated. However, when pedal 12 is pivoted to the elevational down position (FIG. 6), magnetic element 112 is positioned adjacent to magnetic proximity switch 116 and a resultant magnetic field actuates switch 116 to generate an actuation input on line 26 to the selector circuit 16. In response to the actuation input on line 26, selector circuit 16 generates command signals on lines 25, 27 to multi-function device 20 which includes signal receiving circuitry 21 to receive the command signals from selector circuit 16 and produce the appropriate actuation of any mechanical mechanisms corresponding to the selected function. As long as pedal 12 is in the elevational down position (FIG. 6), the foot control device 11 and selector circuit 16 will continue to actuate the multi-function device. To perform the selected function when the pedal 12 is returned to the elevational up position, the device 20 ceases performing the selected function. Alternatively, the system 5 may function so that depressing the pedal 12 initiates the selected function, and device 20 performs the function for a preselected amount of time regardless of whether the pedal remains pivoted down or not.

Figure 7:
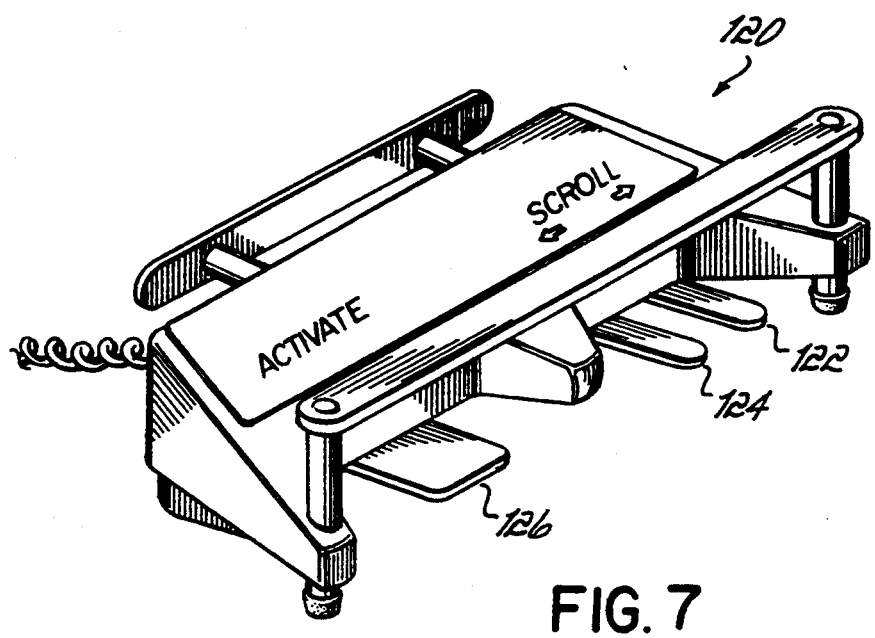
FIG. 7 is a front perspective view of an alternative foot control device for use with the foot-operated control system of FIG. 1.

An alternative embodiment of the foot-operated control device of the present invention is shown in FIG. 7. Control device 120 utilizes a series of different pedals which are depressed to select a function and actuate the selected function. Specifically, pedals 122 and 124 generate selection signals when depressed in order to move the indicator 34 (FIG. 1) to the function menu 18 in opposing directions through menu 18 to select a function. When a function is selected, pedal 126 is depressed to actuate that function. The foot control device contains the necessary internal circuitry to generate selection signals in response to the depression of pedals of 122 and 124 and to generate an actuation signal in response to pedal 126. Similarly, other foot control devices might be utilized with the foot operated control system of the present invention to generate the necessary selection and actuation input signals.

Therefore, the foot-operated control system disclosed herein allows a user to simply and efficiently select a function of a multi-function device and actuate the selected function without an inordinate amount of concentration upon the associated control mechanisms of the system. The foot pedal 12 allows the user's foot to stay generally stationary and has an azimuthal range of motion for selecting a desired function which only requires the user to pivot his foot slightly to the left or to the right. Further, actuation of the selected function is achieved by a simple downward elevational pivot of the foot continued operation. The selection menu allows the user to easily visually determine which function has been selected without focusing his attention away from the more important tasks, such as a surgical operation for example. Additionally, a virtually infinite number of functions are selectable with the present foot control system by using only three motions.

While these and other features of the foot operated control system of the present invention have been described in accordance with preferred embodiments in the invention, it is to be understood that the invention is not limited thereby, and in light of the present disclosure, various other alternative embodiments will be apparent to one of ordinary skill in the art without departing from the scope of the invention. For example, the magnetic elements and magnetic proximity switches utilized in the preferred embodiment of the foot control device might be located in different areas on the base and pedal in accordance with the operation of the invention. Further, additional lateral and elevation movement configurations might be utilized in order to accomplish the objectives of the present invention. Still further, the foot control system might be utilized with any number of different multi-function devices to carry out the desired operation of those devices.

We claim:

1. A foot-operated control device adapted to be connected to a multi-function device to select and actuate the functions of the multi-function device, the control device comprising:

a base with a front end, a rear end, a left side, and a right side;

a foot pedal mounted for azimuthal lateral movement on said base, the foot pedal being mounted for azimuthal lateral movement between a central position and a leftmost position overlying said left side of said base and spaced laterally from said central position and a rightmost position overlying said right side of said base and spaced laterally from said central position:

said foot pedal also being mounted for elevational movement about a horizontal axis mounted to said base, the foot pedal movable about said horizontal base axis between an elevational up position in which a front end of said pedal is at an elevational position above the elevational position of a rear end of said pedal and an elevational down position in which the front end of said pedal is at an elevational position approximately equal to or below the elevational position of the rear end of said pedal;

a first switch located generally on the left side of the base, the first switch being actuated by said pedal in the elevational up position when the pedal is moved azimuthally from said central position to said leftmost position, said actuated first switch producing a first selection signal for selecting a first function of the multi-function device;

a second switch located generally on the right side of the base, the second switch being actuated by said pedal in the elevational up position when the pedal is moved azimuthally from said central position to said rightmost position, said actuated second switch producing a second selection signal for selecting a second function of the multi-function device;

a third switch, the third switch being actuated by said pedal in the central position when the pedal is moved to the elevational down position while in its central position, said actuated third switch producing an activation signal for activating the device, to perform the selected function.

2. The foot-operated control device of claim 1 further comprising an elevational movement inhibitor to prevent the foot pedal from being moved from the elevational up position to the elevational down position when the pedal is moved away from the central position to one of said leftmost and rightmost positions.

3. The foot-operated control device of claim 2 wherein the elevational movement inhibitor comprises a hump section projecting generally vertically from one of the base and the foot pedal, and a generally vertical channel formed in the other one of the base and the foot pedal to receive said hump section when the pedal is in its central position to allow the pedal to be moved to the elevational down position in said central position, the hump section projecting vertically against the pedal when the pedal is at one of the rightmost and leftmost positions to prevent the pedal from being moved to the elevational down position when it is in one of said rightmost and leftmost positions.

4. The foot-operated control device of claim 1 wherein the first, second and third switches each include a magnetic sensor which is operable to activate the respective switch in the presence of a magnetic element, the control device further comprising:

at least one magnetic element mounted on the pedal to be proximate the respective magnetic sensor of one of said first, second, and third switches when the pedal is moved to one of the leftmost position, rightmost position, and elevational down position, respectively, thereby to activate the switch.

5. The foot-operated control device of claim 1, further comprising a yoke coupled to said base, said yoke being elevationally pivotable generally about said horizontal base axis, the pedal pivotally mounted to said yoke to azimuthally pivot on a generally vertical axis with respect to the yoke, wherein the pedal pivots in azimuth and pivots in elevation with respect to said base.

6. The foot-operated control device of claim 1, the pedal being biased to return to said central position when the pedal is not being moved to the left most position or right most position by a user's foot.

7. The foot-operated control device in claim 1, the device being configured such that the pedal returns to the elevational up position when no downward force is applied to said pedal by a user.

8. A foot-operated control system for controlling and operating a multi-function device with the foot, the system comprising:

a selector circuit which is electrically couplable to a multi-function device and is operable for selecting one of at least two functions to be performed by the multi-function device in response to a selection input and is further operable to actuate a multi-function device when such a device is coupled thereto to perform the selected function in response to an actuation input;

a foot-operated control device electrically coupled to the selector circuit, the control device operable to generate said selection and actuation inputs to be electrically input to the selector circuit for controlling a multi-function device, the foot-operated control device comprising:

a base with a front end, a rear end, a left side and a right side;

a foot pedal mounted to move on said base for generating all of said selection and actuation inputs, the foot pedal being mounted for azimuthal lateral movement between a central position and a leftmost position overlying said left side of said base and spaced laterally from said central position and a rightmost position overlying said right side of said base and spaced laterally from said central position, said pedal also being mounted for elevational movement about a horizontal axis mounted to said base, the pedal movable about said horizontal base axis between an elevational up position in which a front end of said pedal is at an elevational position above the elevational position of a rear end of said pedal and an elevational down position in which the front end of said pedal is at an elevational position approximately equal to or below the elevational position of the rear end of said pedal;

an electrical sensor system carried by said base and including signal generating circuits which are responsive to the azimuthal lateral movement of said pedal and are operable to generate a first selection input when the pedal is moved to the leftmost position and a second selection input when the pedal is moved to the rightmost position, the selector circuit operable for receiving said selection inputs and selecting a first function and second function in response to said first selection input and second selection input, respectively;

the signal generating circuits of said sensor system further responsive to elevational movement of the pedal into the elevational down position in the central position and further operable to generate an actuation input, the selector circuit operable for receiving said actuation input and actuating a multi-function device coupled thereto to perform the selected function.

9. The foot-operated control system of claim 8 wherein the electrical sensor system comprises:

a plurality of proximity switches coupled between the pedal and base, the switches being responsive to the location of the pedal with respect to the base to generate said selection and actuation inputs, the plurality of switches including:

a first proximity switch located generally on the left side of the base for generating said first selection input when the pedal is moved azimuthally from the central position to the leftmost position in the elevational up position;

a second proximity switch located generally on the right side of the base for generating said second selection input when the pedal is moved azimuthally from the central position to the rightmost position in the elevational up position; and a third proximity switch located generally in the center of said base for generating said actuation input when the pedal is moved into the elevational down position while in the central position.

10. The foot-operated control system of claim 8 wherein at least three functions may be selected, the system further comprising a function menu electrically coupled to said selector circuit which includes a plurality of visually selectable menu segments, each segment corresponding to a selectable function of a multi-function device, and a visual indicator generated by said selector circuit, said selector circuit operable for visually moving the visual indicator through the selectable menu segments and visually indicating the menu segments and corresponding functions available for selection, the indicator moving in response to said selection inputs;

the selector circuit being responsive to said first selection input to move indicator in discrete, visually-perceptible steps through the segments of the function menu in one direction and responsive to said second selection input to move the indicator in discrete, visually-perceptible steps through the menu segments in another direction, the device function being selected by returning the foot pedal to the central position and stopping movement of the visual indicator when the indicator indicates the desired menu segment, whereafter the function of the selected menu segment is actuated by moving said foot pedal to the elevational down position while in the central position to generate an actuation input.

11. The foot-operated control system of claim 10, the function menu including a translucent plate containing a plurality of individual visual symbols which constitute individual menu segments, each symbol visually indicating a particular selectable function of a multi-function device, the visual indicator including an illumination device to illuminate the translucent plate proximate the chosen symbol and thereby visually indicate which function of the multi-function device has been selected.

12. The foot-operated control system of claim 10 wherein the selector circuit is operable for moving the indicator in discrete, visually-perceptible steps rapidly through the menu segments in the direction corresponding to the pedal position when the foot pedal is maintained in one of its leftmost and rightmost positions for a predetermined amount of time to continuously generate said first and second selection inputs, respectively and thereby scroll the indicator through the menu.

13. The foot-operated control system of claim 8, the foot pedal being biased to return to said central position when the pedal is not being moved to one of the leftmost and rightmost positions by a user's foot.

14. The foot-operated control system of claim 8, the foot pedal mounted to said base such that the pedal returns to the elevational up position when no downward force is applied to said pedal by a user's foot.

15. The foot-operated control system of claim 8, the foot-operated control device further comprising an elevational movement inhibitor to prevent the foot pedal from being moved from the elevational up position to the elevational down position when the pedal is moved away from the central position to one of said leftmost and rightmost positions.

16. A multi-function device capable of performing a plurality of different selectable functions and including at least one mechanical structure operable to execute the selected functions, the device comprising:

a selector circuit operable for selecting one of the plurality of functions of the multi-function device in response to a selection input, the selector circuit further operable for generating a command signal corresponding to a selected function to initiate operation of the mechanical structure of the multi-function device to perform the selected function in response to an actuation input;

a signal receiving circuit electrically coupled to said selector and said mechanical structure, the signal receiving circuit operable for receiving said command signal from the selector circuit and controlling the mechanical structure to execute a selected mechanical function;

a foot-operated control device electrically coupled to the selector circuit, the control device operable for generating said selection and actuation inputs to be electrically input to said selector circuit, the control device comprising:

a base with a front end, a rear end, a left side and a right side;

a foot pedal mounted to move on said base for generating all of said selection end actuation inputs, the foot pedal being mounted for azimuthal lateral movement between a central position and a leftmost position overlying said left side of said base and spaced laterally from said central position and a rightmost position overlying said right side of said base and spaced laterally from said central position, said pedal also being mounted for elevational movement about a horizontal axis mounted to said base, the pedal operable about said horizontal base axis between an elevational up position in which a front end of said pedal is at an elevational position above the elevational position of a rear end of said pedal and an elevational down position in which the front end of said pedal is at an elevational position approximately equal to or below the elevational position of the rear end of said pedal;

an electrical sensor system carried by said base and including signal generating circuits which are responsive to the azimuthal lateral movement of said pedal and are operable to generate a first selection input when the pedal is moved to the leftmost position and a second selection input when the pedal is moved to the rightmost position, the selector circuit operable for receiving said selection inputs and selecting a first function and second function in response to said first selection input and second selection input, respectively;

the signal generating circuit of said sensor system further responsive to elevational movement of the pedal into the elevational down position in the central position and further operable to generate an actuation input, the selector circuit operable for receiving said actuation input and generaing a command signal for the signal receiving circuit for actuating the multi-function device to perform the selected function.

17. The multi-function device of claim 16, further comprising a function menu electrically coupled to said selector circuit which includes a plurality of visually selectable menu segments, each segment corresponding to a selectable function of a multi-function device, and a visual indicator generated by said selector circuit, said selector circuit operable for visually moving the visual indicator through the selectable menu segments and visually indicating menu segments and corresponding functions available for selection, the selector circuit moving said indicator in response to said selection inputs;

the selector circuit being responsive to said first selection input to move the indicator in discrete visually-perceptible steps through the segments of the function menu in one direction and responsive to said second selection input to move the indicator in discrete, visually-perceptible steps through the menu segments in another direction, the device function being selected by returning the foot pedal to the central position and stopping movement of the visual indicator when the indicator indicates the desired menu segment, whereafter the function of the selected menu segment is actuated by moving said foot pedal to the elevational down position while in the central position to generate an actuation input.

18. The multi-function device of claim 17, the function menu including a translucent plate containing a plurality of individual visual symbols which constitute individual menu segments, each symbol visually indicating a particular selectable function of the multi-function device, the visual indicator including an illumination device to illuminate the translucent plate proximate the chosen symbol and thereby visually indicate which function of the multi-function device has been selected.

* * * * *